United States Patent
Nijland et al.

(10) Patent No.: US 8,262,623 B2
(45) Date of Patent: Sep. 11, 2012

(54) ACCESS PORT VALVE ASSEMBLY

(75) Inventors: Peter Lodewijk Joannes Nijland, DE Losser (NL); Berndina Johanna Westenbroek, Losser (NL); Thomas Lambertus Bernardus Nijland, Hengelo (NL)

(73) Assignee: Avesto Tech B.V., Oldenzaal (NL)

( * ) Notice: Subject to any disclaimer, the term of this patent is extended or adjusted under 35 U.S.C. 154(b) by 0 days.

(21) Appl. No.: 12/305,873

(22) PCT Filed: Jun. 20, 2006

(86) PCT No.: PCT/NL2006/000301
§ 371 (c)(1),
(2), (4) Date: Jun. 18, 2010

(87) PCT Pub. No.: WO2007/148959
PCT Pub. Date: Dec. 27, 2007

(65) Prior Publication Data
US 2010/0280456 A1 Nov. 4, 2010

(51) Int. Cl.
*A61M 5/178* (2006.01)
(52) U.S. Cl. .................................. 604/167.03

(58) Field of Classification Search ............... 251/149.1, 251/149.3, 151, 172; 604/167.01–167.04, 604/168.01, 175, 533, 534, 535
See application file for complete search history.

(56) References Cited

U.S. PATENT DOCUMENTS

| 4,436,519 A * | 3/1984 | O'Neill | 604/175 |
| 5,603,702 A * | 2/1997 | Smith et al. | 604/256 |
| 6,238,373 B1 * | 5/2001 | de la Torre et al. | 604/256 |
| 6,551,282 B1 * | 4/2003 | Exline et al. | 604/167.01 |
| 7,789,861 B2 * | 9/2010 | Franer | 604/167.06 |

* cited by examiner

*Primary Examiner* — Christopher D Koharski
(74) *Attorney, Agent, or Firm* — Robert A. Jensen; Jensen & Puntigam, P.S.

(57) ABSTRACT

The invention relates to a valve assembly (20) for use in an access port, in particular a medical access port. The valve assembly comprises a first sealing valve (1) and a second sealing valve (2). The second sealing valve (2) is provided with an annular base (21) and a central member (23) with a central bore (24). The central member (23) is at the outer circumference movably suspended to the annular base (21) by means of a flexible diaphragm (22), which diaphragm (22) is more flexible than the central member (23).
The invention also relates to a medical access port provided with such a valve assembly.

8 Claims, 4 Drawing Sheets

ACCESS PORT VALVE ASSEMBLY

The present invention relates to a valve assembly for use in an access port, in particular a medical access port, comprising a first sealing valve and a second sealing valve.

Medical access ports are commonly used in medical procedures to facilitate the introduction of medical instruments into various interior regions of a patient's body, such as vessels, conduits or cavities.

Generally medical access ports are intended to be introduced into interior regions of a patient's body that include a fluid under pressure. Catheter introducers, for example, are arranged for the introduction of a catheter tube in a blood vessel of a patient. Trocars on the other hand are arranged for the introduction of laparoscopic instruments in the abdomen of a patient being insufflated by means of a gas. Under these circumstances it is essential for the medical access port to allow the introduction of a medical instrument while preventing the pressurized fluid to escape.

In the relevant field medical access ports are known to be provided with a valve assembly comprising a first sealing valve and a second sealing valve. In general the function of the first valve is to prevent fluid flowing out of the valve assembly, when there is no medical instrument present in the medical access port. The function of the second valve is to prevent the outward flow of any fluid present in the valve assembly during the presence of a medical instrument in the medical access port.

It is an object of the invention to provide a valve assembly as mentioned above that facilitates the introduction of medical instruments within a wide range of sizes while maintaining a fluid-tight seal.

According to the present invention this object is achieved by a valve assembly comprising a first sealing valve and a second sealing valve provided with an annular base and a central member with a central bore, wherein the central member is at the outer circumference movably suspended to the annular base by means of a flexible diaphragm, which diaphragm is more flexible than the central member.

The technical measures of the valve assembly according to the invention effectively help to maintain a stable form of the central bore, which is essential to prevent leakage.

Generally the more rigid central bore always keeps shape, while the moveable suspension by means of the more flexible diaphragm provides the suppleness necessary to allow the insertion and withdrawal of medical instruments of varying shapes and sizes. More specifically the larger flexibility of the diaphragm compared to that of the central bore allows for sideways movements of smaller types of inserted medical instruments without deforming the central bore. Additionally the moveable suspension of the central bore supports self-centering of a medical instrument after a non-concentric introduction thereof in the central bore.

According to a first preferred embodiment the diaphragm is a roll-off-diaphragm. Roll-off-diaphragms are known per se in the art. A roll-off diaphragm comprises a curved shape, which defines a convolution. This convolution rolls off when an axial force is applied directly or indirectly to the central member being positioned in the centre of the diaphragm. When a force is exerted radially the curved shape bends. Thus by using a roll-off-diaphragm, hardly any tension or compress stresses occur in the material of the diaphragm, when an instrument is inserted or withdrawn. Furthermore a roll-off-diaphragm moves lightly, corrects for misalignments without too much resistance and is at the same time thick enough to prevent damages and leakages when a sharp medical instrument unintentionally contacts the diaphragm.

In a preferred embodiment the valve assembly is provided with a funnel shaped entrance to the central bore having a wall with a radially outwardly increasing thickness.

The radially outwardly increasing thickness makes the central member according to the invention more rigid in comparison to a central member with a funnel shaped entrance with a constant wall thickness. Consequently the applied forces are better guided to the diaphragm. In addition, the more rigid central bore according to the invention may provide a better resistance against deformation when a medical instrument is introduced or withdrawn, while still allowing easy insertion through the central bore. This allows medical instruments with thicker end portions, for example balloons or grippers holding surgically removed tissue, to be removed easily out of any medical access port provided with this preferred valve assembly according to the invention. Additionally due to the increasing wall thickness the central member is less susceptible to inverting. This is a very important characteristic as an inverted shape renders the medical access port useless. As a direct result of the increasing wall thickness any deformation of the central member will cane stress in the resilient central member which will force the central member to always return to its original shape when a medical instrument is withdrawn.

In a further preferred embodiment the inner wall of the funnel shaped entrance is provided with circumferentially spaced slots. The slots allow the material of the central member to stretch more easily while maintaining strength. Preferably the slots extend radially outward from the central bore thus following the direction of increasing thickness of the wall.

According to a practical preferred embodiment of a valve assembly according to the invention the first sealing valve comprises a generally annular base with a transitional section to a bulging top comprising at least one slit in a central position. Preferably the bulging top is generally dome-shaped. The bulging shape of the top, in particular the dome shape, provides a natural protection against collapse due to the internal pressure difference in the medical access port.

In a further preferred embodiment the bulging to comprises a wall having an, at least partly, radially outwardly increasing thickness. The varying wall thickness offers the same advantages discussed earlier in relation to the second valve, namely that any deformation of the top will cause stress in the resilient top which will force the top to always return to its original shape when a medical instrument is withdrawn. Logically the thinnest part of the top wall is now located in the vicinity of the slit thus allowing a medical instrument to pass the first valve easily. This is especially of importance for thin fragile medical instrument, such as guide wires. These advantageous effects can be even further enhanced by making a generally dome-shaped recess in the inner wall of the bulging top in the region of the slit.

According to another embodiment the first sealing valve comprises two ribs at the outer surface of the bulging top, which ribs are positioned essentially in line, on opposite sides of the slit and perpendicular to the slit. The ribs exert a closing force on the valve lips as a consequence of which the reaction time for closure of the valve lips after withdrawal of a medical instrument is advantageously shortened.

Another embodiment further shortens the reaction time for closing the valve lips by means of a transitional section with radially varying diameters. For example, the projection of the transitional section may be oval or elliptical. In general the valve assembly will be mounted in a cylindrical chamber of a valve housing of a medical access port. When the smallest diameter of the transitional section corresponds to the diameter of the cylindrical chamber, compressing forces will occur due to the larger diameters in the transitional section. Preferably, the direction of the largest diameter in the transitional section is positioned perpendicular to the slit, such that in assembly the valve lips are pressed together.

In a cost-effective embodiment the first sealing valve and the second sealing valve are arranged to be assembled in a snap fit manner.

The invention also relates to a medical access port provided with a valve assembly according to the invention.

These and other features and advantages of the invention will be more apparent with a discussion of a preferred embodiment of the invention and reference to the associated drawings.

The invention will be explained in more detail with reference to the appended drawings, in which.

Figure 1:
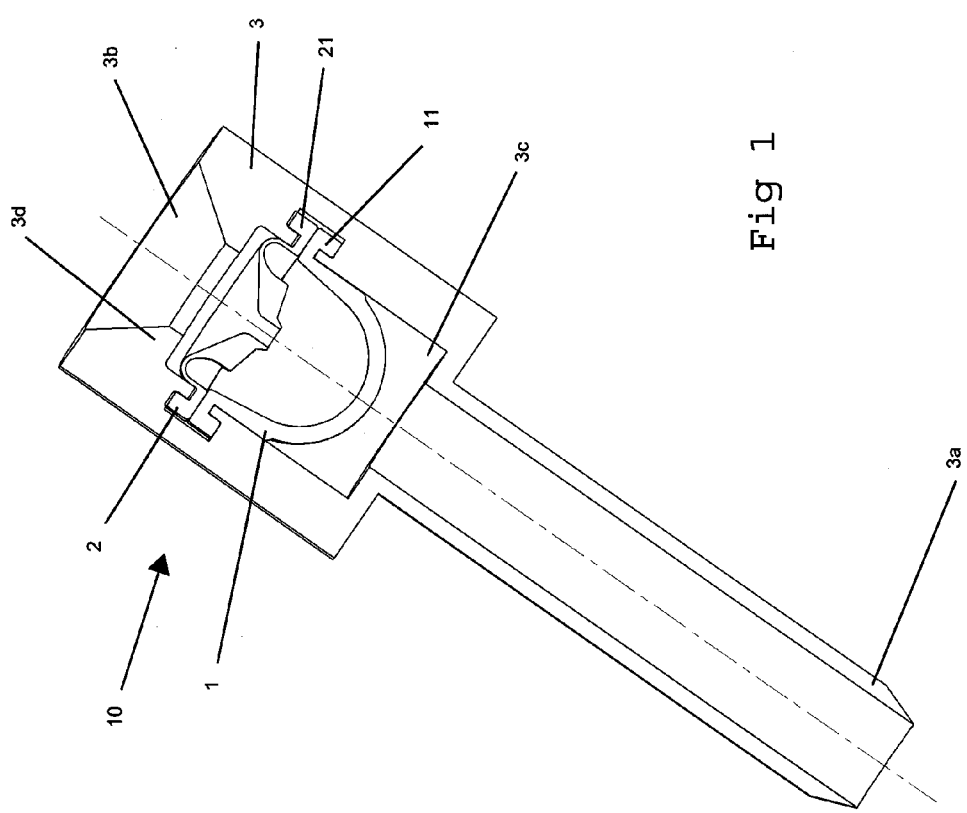
FIG. 1 shows an axial cross-sectional view of a medical access port according to the invention.

FIG. 1 shows an axial cross-sectional view of a medical access port according to the invention. The medical access port 10 has a longitudinally extending valve housing 3 having a passageway there through. The valve housing 3 is generally circular in radial cross-section with locally a larger diameter at the proximal end. The passageway extends from a first aperture 3a at the distal end through a cylindrical chamber 3c up to a second aperture 3b at the proximal end. The edge of the first aperture 3a is sharp for easy insertion in a human or animal body, for example in an artery or in an abdominal wall.

The medical access port 10 is provided with a value assembly according to the invention comprising a first valve 1 and a second valve 2 arranged in an assembled position in the cylindrical chamber 3c. In the embodiment shown the valve assembly comprises adjacent flanges 11, 21 for mounting the sealing valves in the valve housing 3. Each flange has a raised edge at the outer perimeter, which co-operates with a groove in the cylindrical chamber. The flanges are configured such that the sealing valves are firmly held in place in the assembled position such that the valve assembly will not be pushed out of its fitting.

Figure 2:
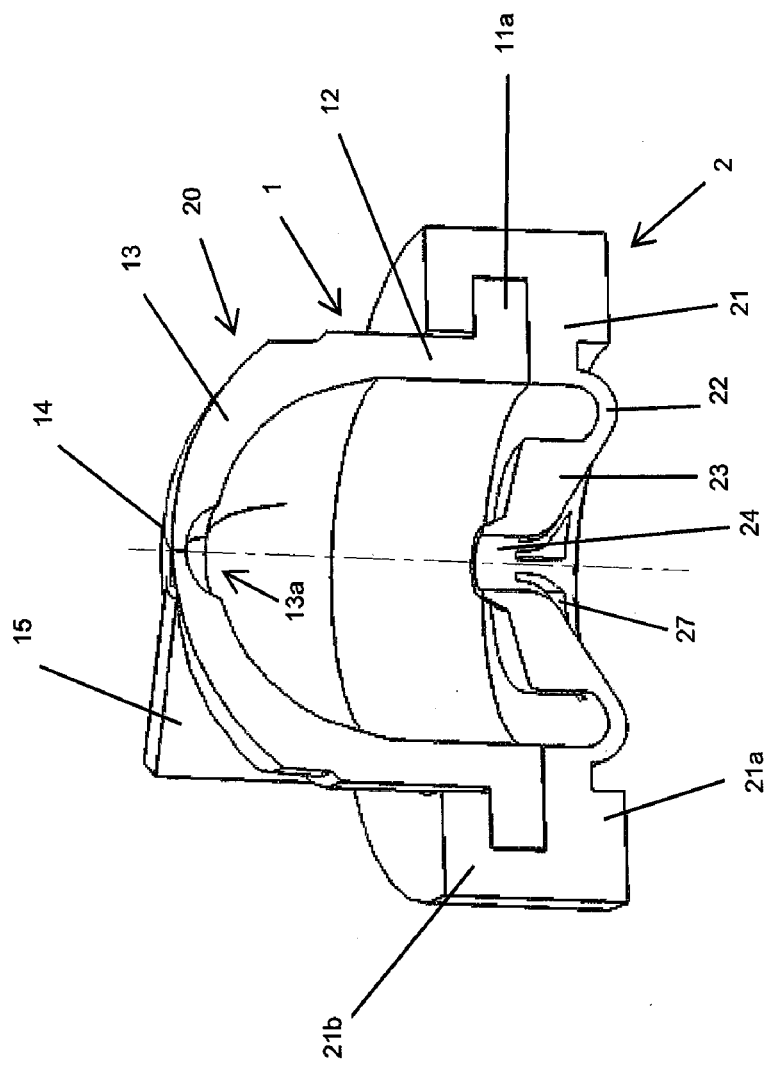
FIG. 2 shows an axial cross-sectional view of a valve assembly according to the invention.

An alternative assembly is shown in FIG. 2. Herein the flange 21 of the second valve 2 is provided with two raised edges 21a and 21b for a snap fit engagement of the outer part 11a of flange 11 of the first valve 1. In this snap fit engagement both sealing valves form one valve assembly and as such are more easily recognizable, and simpler for positioning and assembling in (re-usable) medical access ports by medical personnel.

Due to the funnel shape of the second aperture 3b a medical instrument inserted in the medical access port 10 is automatically centered in front of the second sealing valve 2. The risk of damaging the second sealing valve 2 by the instrument is thus effectively reduced.

The edges of the second aperture 3b define a stop collar 3d intended to limit possible deformation of the second sealing valve 2 when a medical instrument is withdrawn.

The first sealing valve 1 comprises a generally annular base 11 with a transitional section 12 towards a bulging top 13. In the centre of the top a slit 14 defines valve lips adjacent the slit, which open when a medical instrument is introduced and close when the instrument is withdrawn.

The bulging top 13 is generally dome-shaped. The thickness of the wall of the top 13 is thinnest in the vicinity of the slit 14 and increases in the direction away from the slit 14. Typically the thickness of the wall of the top increases from somewhere between 10 and 20% up to 100%. The thinnest region of the top 13 may also be formed by a bulging, more particularly a dome-shaped, recess 13a in the inner wall of the top 13.

Two ribs 15 are positioned essentially in line at the outer surface of the top 13. The ribs lie on opposite sides of the slit 14, essentially perpendicular to the slit 14, such that they exert a closing force thereto.

Figure 3:
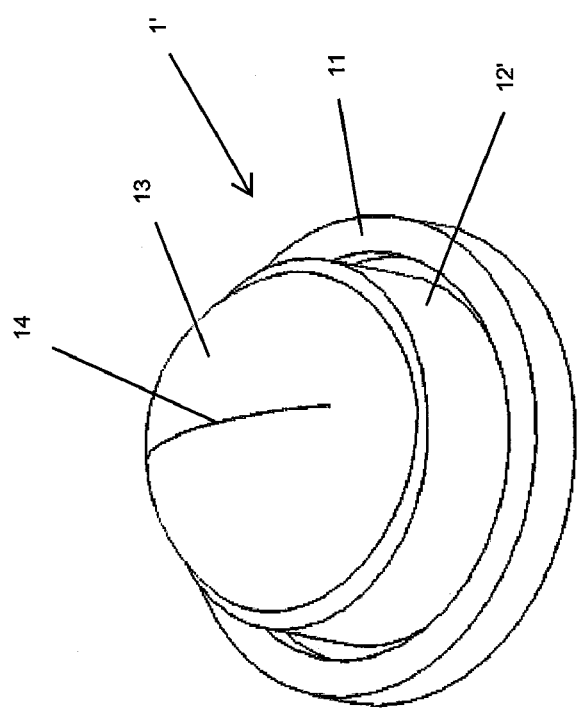
FIG. 3 shows a schematic view of a first sealing valve according to the invention.

In an alternative embodiment of the first sealing valve 1', which is shown schematically in FIG. 3, the ribs 15 are absent. Furthermore the transitional portion 12' has radially varying outer diameters, which in assembly provide a closing force to the slit 14 by being not conform to the inner dimensions of the cylindrical chamber 3c of the valve housing of the medical access port 10. The assembly of the first valve with such a radially non-symmetric transitional portion is fail safe in any access port having a symmetric chamber.

Figure 4:
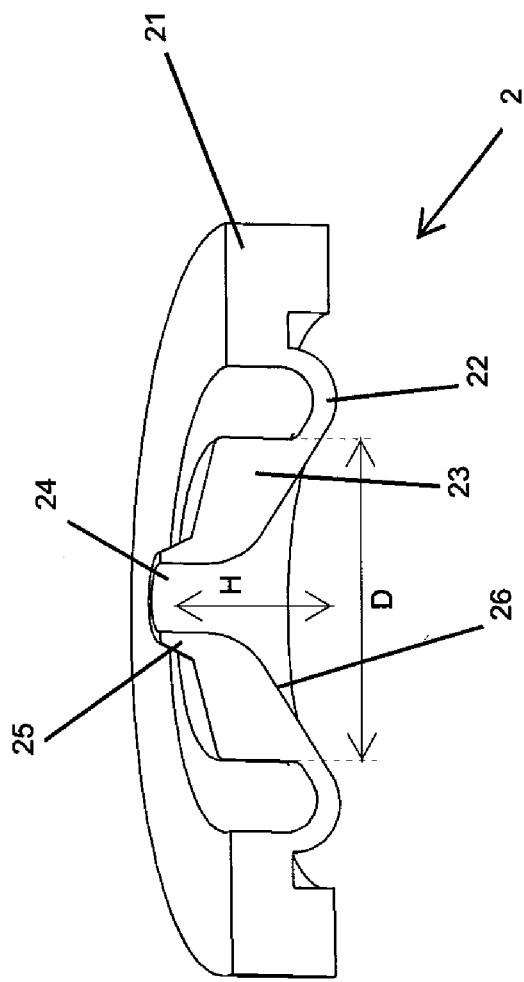
FIG. 4 shows an axial cross-sectional view of a second sealing valve according to the invention.

FIG. 4 shows a perspective cross-sectional view of the second sealing valve 2. The second sealing valve 2 comprises a central member with a central bore 24. The central member 23 is connected to the annular base 21 by a diaphragm 22. At one side the central member 23 comprises a funnel shaped entrance 26 to the central bore 24 for centering a medical instrument introduced therein directly in front of the central bore.

The diaphragm 22 is a roll-off-diaphragm having a curved shape, which defines a convolution. Here, the curved shape is a U-shape. When a radial force is applied the U-shape bends and when an axial force is introduced the U-shape rolls off. As a result, when an introduced medical instrument causes a displacement of the central member generally all deformations are absorbed by the roll-off diaphragm 22 preventing a deformation of the central member 23 itself. The diaphragm 22 is more flexible compared to the central member 23, which is more rigid. To prevent leakage, the rigid central member 23 keeps the shape of the bore 24 stable when a medical instrument is introduced.

Around the edge of the central bore 24 a thin tapered sealing lip 25 is provided. The sealing lip is arranged to fit around the outer surface of an introduced medical instrument to reduce the risk of leakages. Typically, the sealing lip 25 is tapered in a range of 0° to 30°, preferably at most 5°, relative to the central axis.

The central member 23 of the second sealing valve 2 is substantially disk shaped with a height H and diameter D. The dimensions H and D are extreme dimensions of the disk shape measured without the thin sealing lip 25. Preferably, the ratio H/D is at least 0.15. In the illustrated embodiment, the ratio H/D is about 0.5. In practice an optimum is to be found between increasing the stability of the central bore by choosing a higher ratio H/D and decreasing the resistance experienced by insertion or withdrawal of a medical instrument by choosing a lower ratio H/D.

The funnel shaped entrance 26 has a varying thickness that increases in a direction away form the bore 24. Close to the bore 24, that is concentrically positioned in the centre of the central member 23, the wall forming the bore is thick enough to provide a stable shape of the bore.

The inner wall of the funnel shaped entrance 26 is provided with circumferentially spaced slots 27 that extend in a direction away from the central bore 24.

Similar to the first sealing valve, the second sealing valve comprises also a generally annular base 21. The annular bases 11, 21 can engage each other in different ways as discussed earlier.

Preferably, at least the central member is made of an elastomeric material with a high elongation at break and low modulus, such as polyisoprene elastomer. The material of the central member has a value for the elongation at break of at least 700%. Preferably the elongation at break ranges between 800%-1000%. A high elongation at break is advantageous, because this high stretchability improves the sealing of the central member around an introduced medical instrument. The flexible material fits closely for different sizes of medical instruments without tearing.

Preferably the diaphragm is made of a flexible material which is different from the material used for the central member. Preferably it is a material with a high modulus so that the stretch in axial direction during insertion is constrained allowing the housing (of the medical access port) to be short and preventing contact between the central member and the first valve.

A combination of different materials in the second sealing valve could be achieved by co-molding two different materials or molding a fabric into the diaphragm.

To reduce the friction between the valves and the inserted medical instruments, in a preferred embodiment, one or both of the first and the second sealing valves are coated with a dry or wet coating. A suitable low friction surface layer comprises a powder, a grease or oil, e.g. teflon or an inert gel.

Different variants of the preferred embodiments shown are possible within the scope of the invention. In particular the various technical measures of the alternative embodiments of the valve assembly shown in the accompanying figures can be combined to form other alternative embodiments which are to be incorporated herein.

For example, in a modified embodiment the convolution of the diaphragm can be configured as an S-shape in stead of a U-shape.

The first sealing valve may comprise two slits, that intersect to form a cross, which may be utilized instead of a single slit to form a sealing valve having a lip portion, which permits introduction of a medical instrument with much lower introduction forces than for valves having a single slit. This is especially advantageous for thin fragile medical instruments, such as catheters.

In another alternative, the ribs that reinforce the dome shape of the first sealing valve may be positioned at an angle of for example 30° relative to the slit instead of perpendicular to the slit.

As an alternative to the releasable assembly of the two valves, the first and second sealing valve may be bonded to each other, e.g. by being vulcanized or glued.

The medical access port provided with a valve assembly according to the invention is preferably universally suitable for medical instruments within a range of sizes. The valve assembly is designed for cost effective production thus facilitating the use as a disposable article. Since its design allows easy cleaning and (re)-sterilization the valve assembly is also suitable for re-use.

Although the preferred embodiment of the valve assembly has been described in the context of a medical application the invention is not limited thereto. The valve assembly according to the invention is in general suitable for sealing an access port to a compartment that is pressurized by means of a fluid, while allowing an object to be inserted in and withdrawn out of the access port. A person skilled in the art will have no difficulty making small changes to the valve assembly, such as scaling it up, in order to render it suitable for a particular in intended use outside the field of medicine.

The invention claimed is:

1. A valve assembly (20) for use in an access port, in particular a medical access port, comprising:
   a first sealing valve (1); and
   a second sealing valve (2) provided with an annular base (21) and a central member (23) having a wall with a radially outwardly increasing thickness being provided with a funnel shaped entrance (26) to a central bore (24), wherein the central member (23) is at the outer circumference movably suspended to the annular base (21) by means of a flexible diaphragm (22), which diaphragm (22) is more flexible than the central member (23) characterized in that the central member (23) is substantially disk shaped with a height H and diameter D, wherein the ration H/D is at least 0.15 and preferably 0.5, such that the wall forming the bore is thick enough to provide a stable shape of the bore.

2. A valve assembly according to claim 1, wherein the first sealing valve (1) comprises a generally annular base with a transitional section (12) to a bulging top (13) comprising at least one slit (14) in a central position.

3. A valve assembly according to claim 2, wherein the bulging top (13) comprises a wall having an, at least partly, radially outwardly increasing thickness.

4. A valve assembly according to claim 1, wherein the first sealing valve (1) and the second sealing valve (2) are arranged to be assembled in a snap fit manner.

5. A medical access port provided with a valve assembly according to claim 1.

6. A valve assembly according to claim 1, wherein the inner wall of the funnel shaped entrance (26) is provided with circumferentially spaced slots (27).

7. A valve assembly according to claim 6, wherein the slots (27) extend radially outwardly from the central bore (24).

8. A valve assembly according to claim 6, wherein the diaphragm (22) is a roll-off-diaphragm.

* * * * *